United States Patent
Bruzzese

[11] Patent Number: 5,869,714
[45] Date of Patent: Feb. 9, 1999

[54] SALTS OF OMEGA-3-POLYUNSATURATED FATTY ACIDS AND PHARMACEUTICAL FORMULATIONS CONTAINING THEM

[75] Inventor: Tiberio Bruzzese, Milan, Italy

[73] Assignee: Prospa B.V., Gebouw Pluspoint II, Netherlands

[21] Appl. No.: 817,345

[22] PCT Filed: Mar. 22, 1995

[86] PCT No.: PCT/EP95/01075

§ 371 Date: Jun. 11, 1997

§ 102(e) Date: Jun. 11, 1997

[87] PCT Pub. No.: WO96/12696

PCT Pub. Date: May 2, 1996

[30]   Foreign Application Priority Data

Oct. 20, 1994 [NL]   Netherlands ........................... 9401743

[51] Int. Cl.$^6$ ..................................................... C07C 101/00
[52] U.S. Cl. ........................ 554/108; 554/103; 554/223; 554/224; 514/553; 514/554
[58] Field of Search ................................. 554/103, 108, 554/223, 224; 514/583, 584

[56]   References Cited

FOREIGN PATENT DOCUMENTS 640581   3/1995   European Pat. Off. .

*Primary Examiner*—Gary Geist
*Assistant Examiner*—Deborah D Carr
*Attorney, Agent, or Firm*—Walter H. Schneider

[57]   ABSTRACT

Salts of formula $RCOOR'R''_2N^+(CH_2)_nOH$ wherein R represents the alkenyl radical of a $C_{20}$–$C_{22}$ omega-3-polyunsaturated acid; R' represents a hydrogen atom or a $C_1$–$C_2$ alkyl radical; R" represents R', as above defined, or $(CH_2)_nOH$ hydroxyalkyl radical where n is 2 or 3; and their use as cardiovascular agents.

12 Claims, No Drawings

SALTS OF OMEGA-3-POLYUNSATURATED FATTY ACIDS AND PHARMACEUTICAL FORMULATIONS CONTAINING THEM

This application is a 371 of PCT/EP95/01075, filed Mar. 22, 1990.

FIELD OF THE INVENTION

The present invention relates to salts of omega-3 polyunsaturated fatty acids and pharmaceutical formulations containing them.

SUMMARY OF THE INVENTION

In particular, the present invention relates to salts of $C_{20}$–$C_{22}$ omega-3 polyunsaturated acids with aminoalcohols, having the following general formula (I)

wherein:
R represents the alkenyl radical of a $C_{20}$–$C_{22}$ omega-3 polyunsaturated acid;
R' represents a hydrogen atom or a $C_1$–$C_2$ alkyl radical;
R" represents R' as above defined, or a $(CH_2)_nOH$ hydroxyalkyl radical wherein n is 2 or 3.

Long-chain polyunsaturated fatty acids, in particular the omega-3 polyunsaturated acids have been found to be extremely important in the prevention and treatment of various morbid forms, in particular those connected with the cardiocirculatory system (platelet antiaggregatory action, thrombolytic action, antiatheromatous action and so on—see A. Leaf and P. C. Weber, New England J. Medicine, 318, 549, 1988), inflammatory pathologies (S. M. Prescott, J. Biol. Chem., 259, 7615, 1984) and some cancer forms (H. O. Bang et al., Acta Med. Scand., 220, 69, 1976). Marked efficacy was also demonstrated in the treatment of hypertriglyceridemia and hypercholesterolemia, of psoriasis, of immunology, learning and memory disorders, of central and peripheral nervous system pathologies, etc. These activities are often stimulated, at a biochemical level, by competition of the acids in question with arachidonic acid and metabolites originating therefrom through the effect of cyclooxygenase and lipoxygenase enzymes (prostaglandins, prostacyclin, thromboxanes and leukotrienes). In other cases the effect is simply attributed to the accumulation of polyunsaturated acids, replacing acids saturated or with a minor degree of unsaturation, in various organ and cell districts (plasma, platelet and RBC membrane, nervous system etc.).

Of the polyunsaturated fatty acids mentioned above, 4,7,10,13,16,19-cisdocosahexaenoic acid (hereinafter referred as DHA) and 5,8,11,14,17-ciseicosapentaenoic acid (hereinafter referred as EPA) are by far the most important. These acids are also found in marine algae as well as in various microorganisms, but, above all, in fish oils which are at present the commercial source of these polyunsaturated substances. Fish oils are known to contain DHA and EPA in a mixture with saturated and not so unsaturated acids, in the form of triglycerides and it is in this form that the material is at present commercially available for dietary or therapeutic uses (see for instance Maxepa® Seven Seas Health Care Ltd., Hull, England; R. I. Sterling et al., J. Immunol., 139, 4186, 1987). The contents in EPA and DHA in these glycerides is of about 30% expressed as the sum total of the two constituents.

Other dietary or therapeutic preparations of DHA and EPA (W. S. Harris, J. Lipid Res., 30, 785, 1989) were obtained by transesterification of the triglycerides with ethanol and subsequent concentration by different techniques and are therefore used as concentrate mixtures of EPA ethylester and DHA ethylester.

From a pharmaceutical point of view said long chain polyunsaturated fatty acids, as well as, generally speaking, all the derivatives thereof including their ethyl esters, are all extremely water insoluble oils, often dispensed in dosage form of soft gelatin capsules, thus making impossible to attain several pharmaceutically suitable formulations.

The use of organic solvents to incorporate triglycerides and esters in the aqueous phase would be, as such, inadvisable from the toxicological viewpoint and would not permit, at any rate, diluting the preparation in water owing to the consequent separation of the oleaginous phase. In particular, the alkaline and earth-alkaline metal salts, lead to strongly basic solutions, consequently having a poor tolerance, and to the additional disadvantage of a concentration-related pH and an otter uncalled for supply of metal ions.

It has been now surprisingly found that great and unexpected advantages at the level of pharmaceutical technology as well as of a biological and pharmacological type can be attained by using salts of $C_{20}$–$C_{22}$ omega-3 polyunsaturated acids, such as DHA and EPA and their mixtures, with aminoalcohols having the following general formula (I):

wherein:
R represents the alkenyl radical of a $C_{20}$–$C_{22}$ omega-3 polyunsaturated acid;
R' represents a hydrogen atom or a $C_1$–$C_2$ alkyl radical;
R" represents R' as above defined, or a $(CH_2)_nOH$ hydroxyalkyl radical wherein n is 2 or 3.

The compounds so defined often present as thick oils or as low-melting and hardly crystallizing solids, highly water-soluble.

Typical specimens of the salts, subject of the present patent, are DHA and EPA salts with choline hydroxide

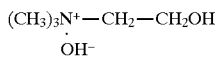

and with ethanolamine $NH_2$—$CH_2$—$CH_2$—$OH$, bases of a physiological type, already ingested with food, hence of absolute pharmacological tolerance.

The salts according to the present invention are prepared, for instance, by contacting said polyunsaturated acid in an aqueous medium with at least one of said aminoalcohols, and finally recovering the desired salt by usual techniques such as evaporation to dryness at low temperature and pressure or by lyophilization.

The salts of the present invention may also be prepared by contacting concentrate alcoholic solutions of said acids with equimolar quantity of said aminoalcohols, and subsequent evaporation of the solution to dryness or precipitation of the salt through dilution with suitable solvents, such as petroleum ether.

Not as easy proves the double-exchange reaction between the acid sodium salt and, for instance, the base hydrochloride. Often salification can be achieved by direct contact, under cooling, so that the two fluid oleaginous constituents gradually thicken as reaction proceeds, rapidly leading to the desired salt.

From the point of view of the pharmaceutical technique, the acquired water-solubility makes it possible to prepare several pharmaceutical formulations, impossible to obtain by using known triglycerides, ethyl esters and the free acids themselves, all extremely water-insoluble. In particular, monophasic formulations in an aqueous medium, such as the liquid forms for oral use, drinkable vials, syrups etc., which would otherwise be impossible to obtain, are readily attained.

The use of the water soluble salts in question is, for the same reason, suited to the preparation of granules, eventually in individual-dose sachets, to be used by oral route following extempore dissolution: the compounds can in fact be incorporated in various solid, water soluble excipients (i.g., saccharose) or enclosed in cyclodextrine, then granulated, in an effervescent form or otherwise, and used after dissolution in water, with no separation of the supernatant oleaginous phases.

The water soluble salts can also be used in formulations for topical use, such as lotions, as well as in injectable preparations intended for parenteral route, with due caution. In the latter case, moreover, DHA and EPA salification with aminoalcohols lead to water solutions with a neutral pH, which is specially convenient as regards local and systemic tolerance of the drug.

Obviously, the DHA and EPA salts in question can be formulated like the commercial triglycerides and ethyl esters as well, which are fluid, water insoluble oils, often dispensed in dosage form of soft gelatin capsules.

The aminoalcohol salts herein claimed can in fact be easily diluted and solubilized with small quantities of the common diluents used in the preparatory technology of soft gelatin capsules, such as triacetin, mixtures of various polyethylene glycols (PEG 200-600+PEG 4000), tween or tween/ethanol mixtures, propylene glycol and several others. In all these cases, the mixture obtained can then be handled as an ordinary oleaginous substance and formulated in soft capsules.

Independently of the foregoing information connected with the improved possibility of formulation by pharmaceutical technique, the salts with aminoalcohols of polyunsaturated acids such as the above mentioned DHA and EPA, afford other fundamental advantages of a biologic, biochemical and pharmacologic type as compared to the same compounds when used in the form of triglycerides, of ethyl esters and also as sodium salts.

It has been surprisingly found that they are better absorbed by oral route as compared to the reference products, consequently affording higher plasma levels than for instance, an equimolecular dose of the corresponding ethyl ester. Better absorption of polyunsaturated acid salts than e.g., esters, is due to the fact that the esters show up, at gastric and enteric levels, as oily droplets, dispersible in the aqueous phase only after formation of local microemulsions, while water soluble salts disperse in a molecular form and are then quickly absorbable in the undissociated equilibrium form. The advantage consequent upon higher plasma levels and the subsequent diffusion in the other districts of the organism, leads to higher concentrations of the polyunsaturated acid in the brain, in the nervous system in general, in the retina and in the other known deposition and accumulation sites.

Specially important is the enrichment in DHA and EPA of the membrane of red cells and platelets to which the polyunsaturated acids confer important hemorheologic (reduction in blood viscosity, increased red blood cell deformability etc.) and antiaggregatory properties respectively.

Salification with special aminoalcohols such as ethanolamine and choline, afford another favourable characteristic to the new salts: these substances in fact are essential constituents of membrane phospholipids, for instance, of erythrocytes and platelets, in the form of phosphatidylethanolamine and phosphatidylcholine and it has been found that both the acid and the base can be absorbed and thereby increase, in a 'synergistic' manner, the two corresponding phospholipid sub-classes mentioned above. Ethanolamine moreover, through endogenous methylating systems, can be methylated to give choline and thereby included in both the above mentioned phospholipid classes.

Phosphatidylserine and phosphatidylinositol are not significantly influenced by administration of the salts subject of this patent.

Considering that the phospholipid class of the erythrocyte membrane, along with the degree of unsaturation of the acyl chains, does condition red cell deformability and blood viscosity, it has been conducted a study to ascertain the effect of the salts in question on erythrocyte phospholipid composition, which we describe hereunder in illustration. 8 healthy volunteers were then selected and divided into 4 groups which were treated by oral route for 3 weeks with a daily quantity of DHA 1.0 g in the form of ethyl ester (1.1 g), sodium salt (1.1 g), choline salt (1.3 g) and ethanolamine salt (1.2 g). Before and after treatment samples of venous blood were collected and sodium citrate added, then the erythrocytes were isolated, washed for 3 times with saline solution (0.15M NaCl, pH 7.4) at 0° and again suspended in saline solution. 1-ml samples from the red cell suspensions were treated with 5 ml of methanol for 10 minutes then with 5 ml of chloroform containing 2 mg/100 ml of the antioxidant 2,6-di-tert.butyl-4-methyl-phenol (BHT). The organic solvents originating from 3 extractions were evaporated to dryness and the residue, formed by the erythrocyte phospholipids, was subjected to bidimensional chromatography according to Turner J. D. and Rouser G., Anal. Biochem. (Part 1—Erythrocyte lipids), 38, 423, 1970 to separate the different phospholipid classes: silica gel 60H (90 g, Merck) plus Fluorisil (7.2 g, BDH Chemicals) plates were used; the solvent systems consisted of chloroform:methanol: 25% ammonia:water (90:54:5.5:5.5) and chloroform:methanol:acetone:acetic acid:water (60:20:80:20:10). The various classes were identified against standard phospolipids (Sigma Chemical). A sample of total phospholipids and the various stains isolated were treated with 1.5 ml of boron trifluoride-methanol for 1 h at 65° C. under nitrogen, to prepare the methyl esters of the acids contained in the phospholipids to undergo gas-chromatography. To this end a Hewlet-Packard 5890 gas-chromatograph was used, fitted with a ionisation flame detector and with an HPl column 25 m in length and 0.31 mm in int. diameter; elium was used as the carrier gas, the injection port temperature was 320° C. and the detector temperature 340° C. The chamber temperature was programmed at 170° C. for 1 min., then increased by 4°°C./min up to 250° C. and kept at this temperature for 15 minutes. It was thus found that phosphatidylserine and phosphatidylinositol differed in their DHA contents by only a small amount as compared to baseline condition (before treatment), while the findings concerning phosphatidylcholine, phosphatidylethanolamine and total phospholipids are shown in table 1.

TABLE 1

Percent increase in DHA content of erythrocyte phospholipids as compared to baseline values

| Phosphollpid ↓ | Treatment (*) --> | | | |
|---|---|---|---|---|
|  | DHA ethyl ester | DHA sodium salt | DHA choline salt | DHA ethanolamine salt |
| Phosphatidylcholine | 77 | 93 | 146 | 113 |
| Phosphatidylethanolamine | 10 | 25 | 38 | 70 |
| Total phospholipids | 56 | 75 | 102 | 103 |

(*) each treatment corresponds to administration of 1 g of DHA for 3 weeks

The foregoing data show that DHA salification through choline and ethanolamine can increase DHA bioavailability as well as its inclusion in the phospholipids of red cell membranes (and then in other districts of the organism such as plasma, platelets, nervous system etc.). In particular, salification through the above mentioned bases can chiefly increase the corresponding phospholipid classes such as phosphatidylcholine and phosphatidylethanolamine.

These favourable characteristics of the salts in question, in terms of absorption and capacity of inclusion in the various phospholipid systems also led to surprising results as regards their pharmacologic activity, such as, e.g., unexpected potent action on inhibition of platelet aggregation in vitro and ex vivo, demonstrated according to known experimental models. Considered however that this action is not fully indicative of the possible therapeutic effects of a drug, we measured the in vivo effect of the new salts in extremely significant tests, by determining for instance, their effect on growth rate of a thrombus induced by a known aggregatory agent (adenosine diphosphate; ADP) in the hamster microvascular system (in vivo antithrombotic action).

Through a different in vivo experimental model also the effect on thrombus formation and disaggregation was evaluated in the hamster, following vascular damage induced by electrical stimulation (thrombolytic action).

In the course of a typical experiment, male hamsters of the Mesocricetus auratus genus, weighing 95–115 g, were acclimatized for 1 week in the laboratory before starting the study, then semi-chronically treated by oral route, for 10 consecutive days with the products under examination. More precisely, the animals were divided into 4 groups: group I received the vehicle alone, group II received DHA ethyl ester 100 mg/kg (equivalent to DHA 92 mg/kg), group III and IV were given DHA 50 mg/kg in the form of ethanolamine salt (59.3 mg/kg) and choline salt (65.7 mg/kg respectively). One hour following the last dose the animals were anaesthetized with sodium pentobarbitone (90 mg/kg, i.p.), the cheek pouch everted with a cotton wool bud and the upper layer and the underlying a vascular connective tissue removed with ophthalmic scissors to expose the lower vascular layer which was then bathed with saline solution and examined under a Leitz Dialux microscope (magnification×250).

Evaluation of the antithrombotic activity requires measuring the growth rate of a thrombus (white body) in the microcirculation induced by the iontophoresis of ADP from a micropipette through the vessel wall. A micropipette of diameter $12\mu$ was filled with $10^{-2}$M solution of ADP connected with a silver/silver chloride reference electrode placed in the animal's mouth and applied to a venule of diameter $16-40\mu$. By applying a negative potential to the micropipette, ADP ($2\times10^{-14}$ moles per second) was injected which caused the formation of a white body (platelet thrombus) gradually growing from the wall of the venule. The growth rate of the thrombus was determined by the time taken for 30%, 50% and 90% of the white body to form, 100% referring to total occlusion of the vessel with stasis. When the current was switched off, the white body rapidly embolised and no new white bodies formed until the current was re-applied. Inhibition of thrombus growth rate was calculated by comparing measurements in treated animals with those obtained in the control group (Table 2).

For the evaluation of the thrombolytic activity a micropipette was filled with 1.0M potassium chloride, applied to an arteriole of diameter $40-60\mu$ and connected to a reference electrode placed in the animal's mouth. A negative potential was applied for 5 seconds using a Grass S48 stimulator to produce a current of 20–30 $\mu$A. A second micropipette containing $10^{-2}$M ADP was applied to the site of electrical damage and a negative potential applied, for 3 seconds. After the current was switched off, the time taken for the resultant thrombus to form and to disaggregate (about 40 seconds) was recorded using a stopwatch. The process of ADP stimulation of the arteriole damaged site was repeated several times and the mean was recorded of the values obtained over one hour and compared with that of the control animals.

The percentage change in the persistence of the thrombus adhering to the damaged site in the treated and untreated animals is therefore an index of the thrombolytic activity of the drug (Table 3).

TABLE 2

Percentage reduction, as compared to the controls, of thrombus growth rate induced by ADP after oral administration of DHA ethyl ester, choline salt and ethanolamine salt over 10 days.

| Post-dose minutes | DHA ethyl ester 100 mg/kg × 10 | DHA choline salt equiv. to DHA 50 mg/kg × 10 | DHA ethanolamine salt equiv. to DHA 50 mg/kg × 10 |
|---|---|---|---|
| 60 | 5.5 | 15.6 | 16.5 |
| 70 | 12.5 | 35.4 | 29.8 |
| 80 | 26.3 | 28.3 | 32.2 |
| 90 | 17.4 | 34.2 | 33.2 |
| 100 | 15.1 | 20.8 | 26.6 |
| 110 | 8.7 | 20.2 | 25.0 |
| 120 | 14.9 | 24.7 | 22.3 |

TABLE 3

Percentage reduction, as compared to the controls, of arteriolar thrombus disaggregation time, after oral administration of DHA ethyl ester, choline salt and ethanolamine salt over 10 days.

| Post-dose minutes | DHA ethyl ester 100 mg/kg × 10 | DHA choline salt equiv. to DHA 50 mg/kg × 10 | DHA ethanolamine salt equiv. to DHA 50 mg/kg × 10 |
|---|---|---|---|
| 60-70 | 21.4 | 31.6 | 30.3 |
| 70-80 | 30.5 | 32.8 | 34.2 |
| 80-90 | 36.2 | 35.4 | 34.5 |
| 90-100 | 32.9 | 37.7 | 38.1 |
| 100-110 | 27.8 | 28.6 | 30.4 |
| 110-120 | 25.9 | 29.1 | 29.8 |

The foregoing data show that DHA ethyl ester is moderately active as an antithrombotic agent in the experimental model adopted while DHA choline and ethanolamine salts are highly active (Table 1), with a percentage reduction in ADP-induced thrombus growth rate of the order of max. 33–34%.

Conversely, DHA ethyl ester is highly active as a thrombolytic agent, exhibiting a percentage reduction in arteriolar thrombus disaggregation time equivalent to 36.2% (Table 2). However DHA choline and ethanolamine salts cause a reduction in disaggregation time of the same order of magnitude (37–38%) following administration of quite lower doses and can therefore be considered definitely more active, if given at the same doses, even in this test.

The overall data reported above make it clear that the aminoalcohol salts of omega-3 polyunsaturated acids, subject of the present invention, can doubtlessly be used as drugs with all therapeutic indications already reported in the literature in so far as their polyunsaturated constituent is concerned (fat-lowering, cholesterollowering, antihypertensive, anti-inflammatory and antitumoral actions; treatment of psoriasis, of pathologies of the retina, of memory, learning and immmunology disorders, and of various affections of the central and peripheral nervous system), but in particular they may be used as platelet aggregation inhibitors (antithrombotic and thrombolytic actions) and in the treatment of related pathologies.

In the various pharmaceutical formulations contemplated, and partly already illustrated, the compounds of the present invention—used as individual active ingredients or as a mixture thereof, or in combination with other drugs—are utilised in doses of from 50 mg to 1 g, preferably from 100 mg to 500 mg, as referred to the polyunsaturated constituent, to be administered once or more times daily.

Administration is possible by any route inclusive of the topical and parenteral routes, but is most frequent per os. The salts of the invention are therefore compounded, either individually or diluted with suitable vehicles or excipients, in soft gelatin capsules or—after adsorption on various materials—in capsules, granules, tablets, or syrups, drops and other liquid forms or even in lotions and creams for topical use, in conformity with the suggestions of common pharmaceutical technology.

DESCRIPTION OF THE PREFERRED EMBODIMENTS

Examples of chemical preparations and of various formulations will be given hereinunder in order to describe the invention in more details, but without limiting in any way the invention itself.

EXAMPLE 1

32.8 g of 4,7,10,13,16,19-cis-docosahexaenoic acid (DHA, purity >90%) are suspended in 140 ml of distilled water and maintained under stirring at room temperature. 24.2 g of 50% w/w of choline hydroxide water solution are then added under cooling, and stirring is continued for 10 minutes up to complete solution. The solution is washed with 50 ml of petroleum ether and evaporated to dryness under reduced pressure and temperature. DHA choline salt is so obtained with a nearly theoretical yield.

The elementary analysis of the product (C,H,N,O,) and the acid and base purity conform to the expected values.

IR spectrum: carboxylate ion peak at 1560 cm$^{-1}$ and 1395 cm$^{-1}$ $^1$H-NMR spectnum (DMSO-d$_6$): δ 5.32 (m, 12H, olefinic H), 3.40 (m, 2H, CH$_2$N$^+$), 3.10 (s, 9H, (CH$_3$)$_3$N$^+$), 2,80 (m, 12H, 6-, 9-, 12-, 15-, 18-CH$_2$; CH$_2$—O), 2.14 (m, 2H, 3-CH$_2$), 2.02 (m, 2H, 21-CH$_2$), 1.91 (t, 2H, 2-CH$_2$), 0.90 (t, 3H, 22-CH$_3$).

EXAMPLE 2

16.4 g of DHA in ethanolic solution are treated with 12.1 g of a 50% w/w choline hydroxide ethanol solution under stirring at room temperature then the solution is decoloured with charcoal and evaporated to dryness at reduced temperature and pressure.

The residue is washed with 50 ml of petroleum ether (b.p. 40°–70° C.) and vacuum-dried thus obtaining DHA choline salt with a nearly theoretical yield.

The physicochemical and analytical characteristics of the product correspond to those given in example 1.

EXAMPLE 3

16.4 g of DHA are treated under stirring with 6.0 g of choline hydroxide while cooling to 0° C. The reaction mixture gradually thickens as salification proceeds and after 10 minutes DHA choline salt isolates, presenting characteristics identical to those of the product obtained in the preceding examples.

EXAMPLE 4

32.8 g of DHA (purity >90%) are suspended in 160 ml of distilled water and treated under stirring with 6.1 g of ethanolamine. The solution is maintained under stirring for 10 minutes, then washed with 50 ml of petroleum ether and evaporated to dryness at reduced pressure and temperature: 38.5 g of DHA ethanolamine salt is obtained.

The elementary analysis of the product and the acid and base purity conform to the expected values.

IR spectrum: carboxylate ion peak at 1550 cm$^{-1}$ and 1400 cm$^{-1}$ $^1$H-NMR spectrum (DMSO-d$_6$) δ 5.32 (m, 12H, olefinic H), 3.48 (t, 2H, CH$_2$N$^+$), 2.80/2.71 (m, 12H, 6-, 9-, 12-, 15-, 18-CH$_2$; CH$_2$O), 2.18 (m, 2H, 3-CH$_2$), 2.00 (m, 4H, 2-CH$_2$ and 21-CH$_2$), 0.90 (t, 3H, 22-CH$_3$).

EXAMPLE 5

38.2 g of DHA are maintained under slow stirring and dropwise added with 6.1 g of ethanolamine, cooling to 0° C. The oleaginous mixture gradually thickens with consequent formation of the corresponding salt. After 10 minutes under stirring, the homogeneous reaction 20 mass is totally water-soluble and identical, as far as analysis is concerned, to the DHA ethanolamine salt described in example 4.

EXAMPLE 6

30.2 g of 5,8,11,14,17-cis-eicosapentaenoic acid (EPA, purity >90%) are treated with 12.1 of choline hydroxide according to one of the procedures described in examples 1 to 3. After charcoal treatment EPA choline salt is thus obtained with a nearly theoretical yield. The product is water-soiuble and its physicochemical and analytical characteristics conform to the expected values.

EXAMPLE 7

30.2 g of EPA are treated with 6.1 g of ethanolamine according to the procedure described in examples 4 and 5. 36.2 g of EPA ethanolamine salt is obtained which is highly water-soluble and fairly pure to the analysis.

EXAMPLE 8

0.1 moles of DHA are treated with choline hydroxide (0.05 moles) and with ethanolamine (0.05 moles) according to one of the preceding examples. A DHA mixed salt of choline and ethanolamine is thus obtained with a high yield.

EXAMPLE 9

0.05 moles of DHA and 0.05 moles of EPA are reacted with 0.1 mole of choline, according to one of the preceding examples.

A high yield of DHA and EPA mixed choline salt is obtained.

EXAMPLE 10

By operating in accordance with one of the procedures described in the foregoing examples, but by using the suitable acid and the suitable base, the following salts are obtained:

DHA propanolamine salt
DHA N,N-dimethyl-ethanolamine salt
DHA diethanolamine salt
DHA triethanolamine salt
EPA N,N-dimethyl-ethanolamine salt
EPA diethanolamine salt
EPA triethanolamine salt

EXAMPLE 11

| Formulation in gelatin capsules | |
|---|---|
| DHA choline salt (394.2 mg), equivalent to DHA | 300 mg |
| Triacetin | 100 mg |
| Gelatin | 127 mg |
| Glycerol | 62 mg |
| Ethyl p-hydroxybenzoate sodium | 0.58 mg |
| Propyl p-hydroxybenzoate sodium | 0.29 mg |
| Vitamin E | 1 mg |

EXAMPLE 12

| Formulation in gelatin capsules | |
|---|---|
| DHA choline salt (131.4 mg), equivalent to DHA | 100 mg |
| Triacetin | 40 mg |
| Gelatin | 65 mg |
| Glycerol | 32 mg |
| Ethyl p-hydroxybenzoate sodium | 0.3 mg |
| Propyl p-hydroxybenzoate sodium | 0.15 mg |
| Vitamin E | 0.5 mg |

EXAMPLE 13

| Formulation in gelatin capsules | |
|---|---|
| EPA choline salt (402.3 mg), equivalent to EPA | 300 mg |
| Triacetin | 90 mg |
| Gelatin | 127 mg |
| Glycerol | 62 mg |
| Ethyl p-hydroxybenzoate sodium | 0.58 mg |
| Propyl p-hydroxybenzoate sodium | 0.29 mg |
| Vitamin E | 3.00 mg |

EXAMPLE 14

| Formulation in gelatin capsules | |
|---|---|
| DHA ethanolamine salt (592.9 mg) equivalent to DHA | 500 mg |
| Polyethylene glycol 300 | 200 mg |
| Gelatin | 170 mg |
| Glycerol | 83 mg |
| Ethyl p-hydroxybenzoate sodium | 1 mg |
| Propyl p-hydroxybenzoate sodium | 0.5 mg |
| Vitamin E | 1 mg |
| Ascorbyl palmitate | 2.5 mg |

EXAMPLE 15

| Formulation in gelatin capsules | |
|---|---|
| EPA ethanolamine salt (360.6), equivalent to EPA | 300 mg |
| Polyethylene glycol 300 | 130 mg |
| Gelatin | 127 mg |
| Glycerol | 62 mg |
| Ethyl p-hydroxybenzoate sodium | 0.58 mg |
| Propyl p-hydroxybenzoate sodium | 0.29 mg |
| Vitamin E | 1 mg |

EXAMPLE 16

| Formulation in gelatin capsules | |
|---|---|
| DHA choline salt (197.1 mg), equivalent to DHA | 150 mg |
| DHA ethanolamine salt (177.9 mg), equivalent to DHA | 150 mg |
| Polyethylene glycol | 120 mg |
| Gelatin | 130 mg |
| Glycerol | 64 mg |
| Ethyl p-hydroxybenzoate sodium | 0.6 mg |
| Propyl p-hydroxybenzoate sodium | 0.3 mg |
| Vitamin E | 1 mg |

EXAMPLE 17

| Formulation in gelatin capsules | |
|---|---|
| DHA ethanolamine salt (177.9 mg), equivalent to DHA | 150 mg |
| EPA ethanolamine salt (180.3 mg), equivalent to EPA | 150 mg |
| Propylene glycol | 130 mg |
| Gelatin | 130 mg |
| Glycerol | 64 mg |
| Ethyl p-hydroxybenzoate sodium | 0.6 mg |
| Propyl p-hydroxybenzoate sodium | 0.3 mg |
| Vitamin E | 0.3 mg |
| BHT | 0.15 mg |

EXAMPLE 18

| Formulation in syrup form | |
|---|---|
| DHA choline salt (3.94 g), equivalent to DHA | 3 g |
| Saccharose | 50 g |
| Methyl p-hydroxybenzoate | 0.075 g |
| Ethyl p-hydroxybenzoate | 0.029 g |
| Propyl p-hydroxybenzoate | 0.021 g |
| Sodium ascorbate | 0.100 g |
| Orange flavouring | 0.250 g |
| Purified water q.s. ad 100 ml | |

EXAMPLE 19

| Formulation in drops | |
|---|---|
| DHA ethanolamine salt (35.58 g), equivalent to DHA | 30 g |
| Methyl p-hydroxybenzoate | 0.090 g |
| Ethyl p-hydroxybenzoate | 0.035 g |
| Propyl p-hydroxybenzoate | 0.025 g |
| Sodium metabisulfite | 0.300 g |
| Orange flavouring | 2 g |
| Purified water q.s. ad 100 ml | |

EXAMPLE 20

| Formulation in lotion | |
|---|---|
| DHA choline salt (13.14 g) | 10 g |
| Ethanol | 30 g |
| Sodium metabisulfite | 0.3 g |
| Pouce perfume | 0.6 g |
| Purified water q.s. ad 100 ml | |

EXAMPLE 21

| Formulation in oral individual-dose granules (extempore dissolution) | |
|---|---|
| DHA ethanolamine salt (1185.8 mg) equivalent to DHA | 1000 mg |
| Precipitated silica | 50 mg |
| Lemon flavouring | 100 mg |
| Sorbitol q.s. ad | 5 g |

EXAMPLE 22

| Formulation in tablets for oral use | |
|---|---|
| DHA ethanolamine salt (296.5 mg) equivalent to DHA | 250 mg |
| Precipitated silica | 50 mg |
| Microcrystalline cellulose | 100 mg |
| Talc | 10 mg |
| Magnesium stearate | 5 mg |
| Lactose | 133.5 mg |

I claim:

1. Salts of $C_{20}$–$C_{22}$ omega-3 polyunsaturated acids with aminoalcohols, having the following general formula (I)

$$R-COO^- \ R'R''_2N^+-(CH_2)_n-OH \qquad (I)$$

wherein:

n is 2 or 3

R represents the alkenyl radical of a $C_{20}$–$C_{22}$ omega-3 polyunsaturated acid;

R' represents a hydrogen atom or a $C_1$–$C_2$ alkyl radical;

R" represents R' as above defined, or a $(CH_2)_nOH$ hydroxyalkyl radical where n is 2 or 3 provided that when R' is hydrogen, R" is not $(CH_2)_2OH$.

2. A salt according to claim 1, wherein the polyunsaturated acid is the 4,7,10,13,16,19-cis-docosahexaenoic acid or the 5,8,11,14,17-cis-eicosapentaenoic acid or a mixture thereof.

3. A salt according to claim 1, wherein the aminoalcohol is ethanolamine, N-methyl-ethanolamine, N,N-dimethyl-ethanolamine, choline, diethanolamine, propanolamine, dipropanolamine or a mixture thereof.

4. A salt according to claim 2, which is the 4,7,10,13,16,19-cis-docosahexanoic acid choline salt.

5. A salt according to claim 2, which is the 4,7,10,13,16,19-cis-docosahexanoic acid ethanolamine salt.

6. A salt according to claim 2, which is the 5,8,11,14,17-cis-eicosapentanoic acid choline salt.

7. A salt according to claim 2, which is the 5,8,11,14,17-cis-eicosapentanoic acid ethanolamine salt.

8. A salt according to claim 2, which is the 4,7,10,13,16,19-cis-docosahexanoic acid choline and ethanolamine mixed salt.

9. A salt according to claim 2, which is the 4,7,10,13,16,19-cis-docosahexanoic acid and the 5,8,11,14,17-cis-eicosapentanoic acid mixed choline salt.

10. A salt according to claim 2, which is the 4,7,10,13,16,19-cis-docosahexanoic acid and the 5,8,11,14,17-cis-eicosapentanoic acid mixed ethanolamine salt.

11. A pharmaceutical composition endowed with anti-thrombotic and thrombolytic activities which comprises as the principal active ingredient an effective amount of a salt according to claim 2 together with a pharmaceutically acceptable carrier.

12. A process for the treatment of cardio-vascular diseases which comprises orally administering to a patient an effective amount of a composition according to claim 11.

* * * * *